United States Patent [19]
Shukla

[11] Patent Number: 5,340,449
[45] Date of Patent: Aug. 23, 1994

[54] APPARATUS FOR ELECTROELUTION

[76] Inventor: Ashok K. Shukla, 4676 Smokey Wreath Way, Ellicott City, Md. 21043

[21] Appl. No.: 965,862

[22] Filed: Oct. 23, 1992

Related U.S. Application Data

[63] Continuation-in-part of Ser. No. 623,875, Dec. 7, 1990, abandoned.

[51] Int. Cl.$^5$ .................. B01D 57/02; B01D 61/42
[52] U.S. Cl. .................. 204/180.1; 204/182.1; 204/182.3; 204/182.8; 204/299 R; 204/301
[58] Field of Search ............ 204/180.1, 182.1, 182.3, 204/182.8, 299 R, 301

[56] References Cited
U.S. PATENT DOCUMENTS

4,707,233 11/1987 Margolis .................. 204/182.3

Primary Examiner—John Niebling
Assistant Examiner—Arun S. Phasge
Attorney, Agent, or Firm—Max Stul Oppenheimer

[57] ABSTRACT

This invention involves the elution of macromolecules such as proteins, deoxyribonucleic acid(DNA), ribonucleic acid(RNA) from solid phase matrix such as polyacrylamide, agarose and membranes such as polyvinyl difluoride (PVDF) in an electric field. The elution chamber shown in FIG. 1 consists of two separate screws 9, 9a and attachable chamber 1. The screw well 8 holds the gel matrix containing the macromolecules and is separated by the bottom chamber 1 with a membrane 5 with a nominal molecular weight cutoff higher than the macromolecule. On the other hand, the macromolecule is retained in the well 1 by introducing another membrane 6 having a molecular weight cutoff lower than the molecular weight of the macromolecule. Alternatively, macromolecules separated on membrane, e.g. PVDF, are held in a Teflon or plastic membrane holder 11. This holder can fit inside well 8 in screw 9. In addition, chamber 1 contains a well 7. The macromolecules migrate through the electrophoretic field and are concentrated in well 7. Since the volume of the well 7 is predetermined 10 μl—one ml or more), results in concentration of the macromolecules. Next, the chamber 1 is unscrewed from the top screw 8 and closed with a screw without a hole 13, and the entire device is submerged into a dialysis buffer. Following dialysis for a given time, the fluid above the bottom screw 9a itself and the membrane beneath it are removed. The sample is taken out from hole 7. If further concentration of the sample is required, then following removal of the fluid above the screw 9a, the entire device is transferred to a vacuum desiccator and concentrated to any desired volume.

17 Claims, 5 Drawing Sheets

APPARATUS FOR ELECTROELUTION

This application is a continuation-in-part of application Ser. No. 623,875, filed Dec. 7, 1990 now abandoned.

BACKGROUND OF THE INVENTION

This invention relates to a device and method for the isolation of macromolecules (including proteins and nucleic acids) from a gel or other polymer supports (or also in solution) to a predetermined volume (10 ul to one ml or more). Furthermore, the macromolecule can be dialyzed and concentrated in the same device.

Electrophoresis traditionally involves establishing an electric field between opposite ends of a solid gel matrix made of agarose and/or polyacrylamide, cellulose acetate. The sample (usually a protein or nucleic acid) is applied on one end of the gel and subjected to electrophoresis. Depending upon various physicalchemical characteristics, the sample migrates through the electrical field at a particular velocity. After electrophoresis, the gel is removed, stained with reagents specific for proteins and/or nucleic acids, destained with organic solvent mixtures and photographed. Whereas electrophoretic separation of macromolecules is an established technique, the elution of macromolecules from the gel is a difficult nonreproducible procedure. Such macromolecules are of potential commercial value because of their applications in science and medicine. Over the last decade or so, various attempts have been made to sluts such macromolecules from gels.

Perhaps the simplest procedure for the elution of macromolecules involves washing the gel and vigorously mixing it with a solution containing salt for several hours. Next, the entire mixture is centrifuged. The macromolecule eluted with the salt solution is precipitated with ethanol. This procedure is very time-consuming and the recovery of macromolecules varies considerably depending upon the nature of the macromolecule. Moreover, ethanol precipitation results in denaturation of several proteins or loss of biological activity of macromolecules.

A similar approach has been taken to elute nucleic acids from agarose gels. Here, agarose gel is melted by heating to 65° C. The mixture is extracted with phenol and the samples eluted. As expected, recoveries are usually low with this procedure. In addition, phenol is a highly toxic and biohazardous substance.

Since diethylaminoethyl(DEAE) cellulose binds deoxyribonucleic acid (DNA), it has been employed to elute DNA from gels. The procedure involves i) electrophoretic transfer of DNA from gels to DEAE-paper. ii) alternatively, DEAE-paper is inserted into slots immediately under each band, thus DNA is transferred electrophoretically. Although these procedures yield excellent recoveries, they are highly dependent on technique and the apparatus is expensive.

Decomposing the gel with chemicals, followed by trapping the macromolecules on glass beads and their elution with salt solution is another method of elution. However, this method is dependent on buffer conditions.

In 1985, Kartenbech introduced an electroelution apparatus (U.S. Pat. No. 4,552,640). This apparatus consists of an upper electrode in the upper chamber and the lower chamber to hold buffer solution and a lower electrode. The upper chamber is separated from the lower chamber by a septum, and the two chambers are connected by a connecting passage within the septum. The end of the lower chamber holds a dialysis membrane, wherein the electrophoretically eluted protein or polypeptide is collected. There are several disadvantages with this apparatus. These are: i) since the volume of the lower chamber is large, it results in dilution of the sample, and ii) since the surface area of the dialysis membrane is large it results in non-specific adsorption of macromolecules resulting in very low recoveries.

In 1985, Walsh introduced an apparatus to sluts nucleic acids (U.S. Pat. No. 4,545,888). This apparatus has features to introduce multiple copies of transfer chamber, filter discs to hold DEAE cellulose and negative electrode. Basically, in this procedure the sample is electrophoresed and collected on DEAE resin (held by a filter disc) at the bottom end of the lower chamber. Next, the filter disc is removed and DNA eluted from the resin employing standard elution protocols. This procedure requires an additional step involving the slution of nucleic acids from DEAE. Moreover, its application to elute proteins and polypeptides is uncertain.

In 1987, Burd introduced an electroelution method and apparatus (U.S. Pat. No. 4,699,706). This apparatus has features in which the electroeluted sample passes through a glass frit and is collected in a semipermeable membrane at the bottom end of the lower chamber. Some of the disadvantages of this apparatus are: i) the dialysis membrane must be held in place by a retaining ring, a gasket and internal shoulders built in the equipment. There are several disadvantages with this equipment. For example, i) this is a rather complex setup and the success depends upon the technique, ii) because the dialysis membrane is smaller then the diameter of the glass frit, it results in poor recovery, iii) use of dialysis membrane results in non specific adsorption of macromolecules, which also contributes to low recovery. iv) there is no possibility of capping the columns to harvest the sample collected in the membrane, v) when the sample cup is removed, it leads to the disruption of the sample collected as it leaks through the filter disc and/or fluid held in the sleeve holding the cup.

In 1986, Clad introduced an apparatus for electroeluting macromolecules from gel (U.S Pat. No. 4,608,147). This apparatus contains an upper chamber which holds a permeable membrane (pore size about 0.2 micro meter) through which macromolecules can migrate downstream. The sample is collected in the lower chamber on top of an impermeable membrane having a molecular weight greater than 1000. Following elution, the polarity of the electric field is reversed for 10 to 15 seconds, so that the macromolecules adsorbed to the inner surface of the outer membrane are released from the membrane into the trap space. There are several disadvantages of this apparatus. These are: i) the use of an impermeable membrane in the lower chamber results in dilution of sample, thus requiring concentration further, ii) because the sample is contaminated with the electrophoretic buffer, an additional step (e.g. dialysis) is required to remove such contaminants.

In 1990, Brautigam and Gorman introduced an electroelution apparatus (U.S. Pat. No. 4,964,961). This equipment consists of a tapered tube divided by a porous disc into an open upper section and a lower section which can be closed by a removable cap. The equipment has a dialysis membrane equal to the diameter of the removable cap and is affixed to it to close off the lower section. After electroelution, the upper section is closed. The sample is collected through the cup and dialysis membrane at the bottom end of the tube. The disadvantages of this equipment are: i) the sample is contaminated and diluted with the electrophoretic buffer; accordingly, it requires dialysis and concentration, further adding to the time effort for such procedures, and ii) non-specific adsorption of sample to the dialysis membrane results in loss of recovery.

In summary, at the present time the separation of macromolecules from a solid phase matrix involves procedures that are elaborate, labor-intensive, expensive, and yields are poor. Such equipment does not have dialysis capabilities resulting in considerable loss of precious macromolecules. In addition, the handling of samples subjects the investigator to a higher chance of contamination with macromolecules. For example, the elution of radiolabeled macromolecules, toxins, and viruses involves electrophoresis resulting in contamination of the apparatus with unbound radioactive material. The eluted protein is usually repeatedly centrifuged against a membrane filter or precipitate in a concentrated salt solution. The resulting material is next dialyzed in a bag which results in removal of salts and at the same time increases the sample volume. Such a sample is next concentrated by ultrafiltration. Taken together, all of these procedures are time-consuming, and often the yields are low (10–30%) compared to the starting material. Furthermore, dialysis and concentration (if required) of the sample are additive steps required to prepare samples, which result in further low recoveries.

DETAILED DESCRIPTION AND PREFERRED EMBODIMENTS

Figures 1, 2:
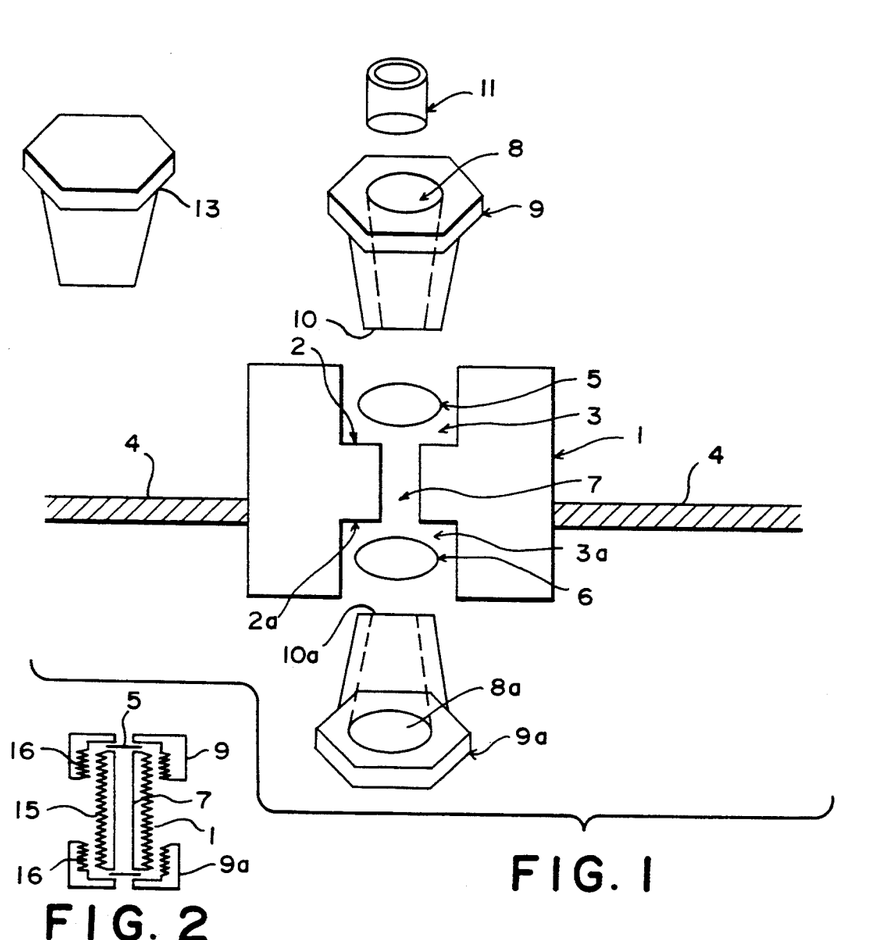
FIG. 1 shows an expanded view of one embodiment of the electroelution device according to the present invention.
FIG. 2 shows the chamber of the electroelution device having threads to cooperate with threaded screws in accordance with the present invention.

The present invention relates to an electroelution device for the elution of macromolecules from a support. The macromolecules may be nucleic acids, proteins or carbohydrates. The support may be a gel, nitrocellulose, polyvinyl difluoride or the like. Referring to FIG. 1, the chamber 1 is made of any suitable plastic material, including but not limited to plastic or glass. Suitable plastics include Teflon, acrylics and the like. The outer surface of chamber 1 can be conical, round or any other shape. For example, the chamber can be cylindrical for use with a round gasket to prevent leakage. Further, the chamber can have a cubical or rectangular shape to prevent it from rotating or rolling away from a specific position within a tank or other container. The outer surface must be smooth so that it can fit in electrophoresis tank plate 4. It is necessary that a tight seal be made between the chamber 1 and plate 4. This seal can be accomplished by tapered hole, sealing ring or by gasket. The electrophoresis tank plate 4 separates the two electrode (cathode and anode) compartments (FIG. 3) in electrophoresis tank 14. These compartments are filled with the buffer or solution of choice.

Referring additionally to FIG. 1, the chamber 1 has a through-hole 7, which can be of different sizes and diameters. This hole determines the elution volume of the macromolecule. On both sides of the hole 7, there are bigger holes (wells) 3 and 3a, which are tapered at the side. The well surfaces 2 and 2a are smooth so that they can hold membranes 5 and 6. The membranes 5 and 6 can be the same or a different type, such as different materials or a different molecular size exclusion, described below. These membranes can be of different materials, e.g., cellulose acetate, nitrocellulose, PVDF, Teflon, etc. The membrane 6 is semipermeable and holds macromolecules. The small molecules can pass through depending on the molecular weight cutoff of these membranes. Membrane 5 can be a frit or filter membrane, which allows the passage of macromolecules. By using a membrane filter having a particular molecular weight cutoff the membrane will retain macromolecules higher than its molecular weight cutoff. On the other hand, it will allow the passage of molecules of a similar or lower molecular weight than the molecular weight cutoff of the membrane. Membranes 5, 6 can be placed at platform 2 and 2a, respectively, via a tapered screw 9, 9a. The screws 9, 9a and the chamber can be joined, for example, by a threaded fitting (as depicted in FIG. 1) or by a tapered quick-fit or snap-type fitting. In addition, the chamber 1 can be provided with threads 15 on its exterior to cooperate with threads 16 on the screws 9, 9a, as shown in FIG. 2. This configuration is advantageous, for it positions the membranes 5, 6 in close contact with the liquid in the tank to allow for faster interaction.

The screws 9, 9a are tapered to fit the holes 3, 3a, so that they can be screwed into the holes 3, 3a, respectively. Screws 9, 9a are made of the same or a compatible material as the chamber 1. Screws 9, 9a have a smooth surface 10, 10a which fit on the membrane 5 or 6 and tighten on the surface 2, 2a in such a way that no fluid can leak from the hole 7. The leak-proof/tightener can also be achieved by using an O-ring. The membranes 5, 6 have the same diameter as the surface 10 or 10a. By way of example, the volume of the chamber can be as low as 1 microliter to 1 milliliter for analytical purposes, or up to 1 liter or larger for preparative purposes. The diameter of the screw and membrane platform can be from about 0.5 cm to about 10 cm, or larger.

Figure 3:
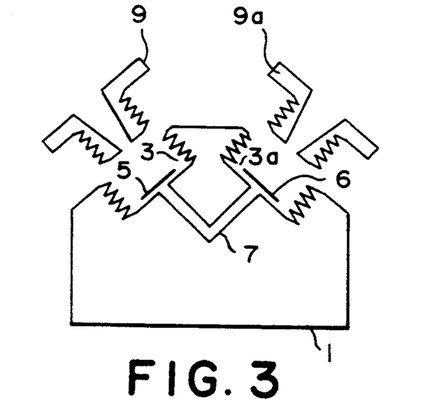
FIG. 3 and 4 show expanded views of different configurations of the electroelution device of the present invention.
Figure 4:
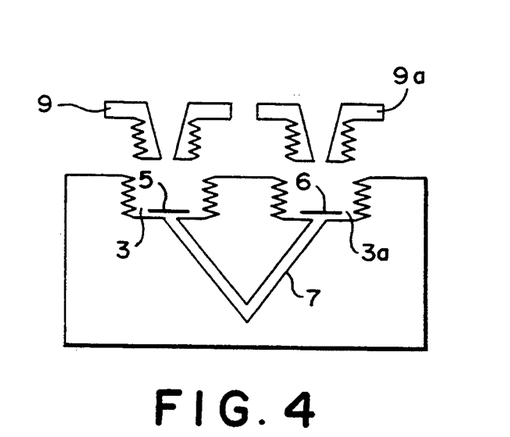

Screw 9 or 9a has a through-hole 8 or 8a, respectively. The hole 8 or 8a can be conical or cylindrical, and can be of different size or shape. The hole 8 serves as a cavity to hold the gel piece or macromolecules on other supports. The holder 11 is made of the same or a compatible material as the chamber 1, and has an outer diameter smaller than the diameter of hole 8 so that it can fit inside the hole 8. This holder 11 can hold the gel piece or membrane, e.g., PVDF (which would otherwise float and can not be retained inside the hole 8 without any support). Screw 13 is the same as screw 9 but does not have a through-hole 8. Screw 13 is used for the closing hole 3 during the dialysis. With reference to FIGS. 3 and 4, the holes 3, 3a and the hole 7 in the chamber 1 can be arranged in various orientations with respect to each other. For example, the holes 3, 3a can be perpendicular (FIG. 3) or coplanar (FIG. 4) and the hole 7 can be disposed at an angle therebetween.

Figure 5:
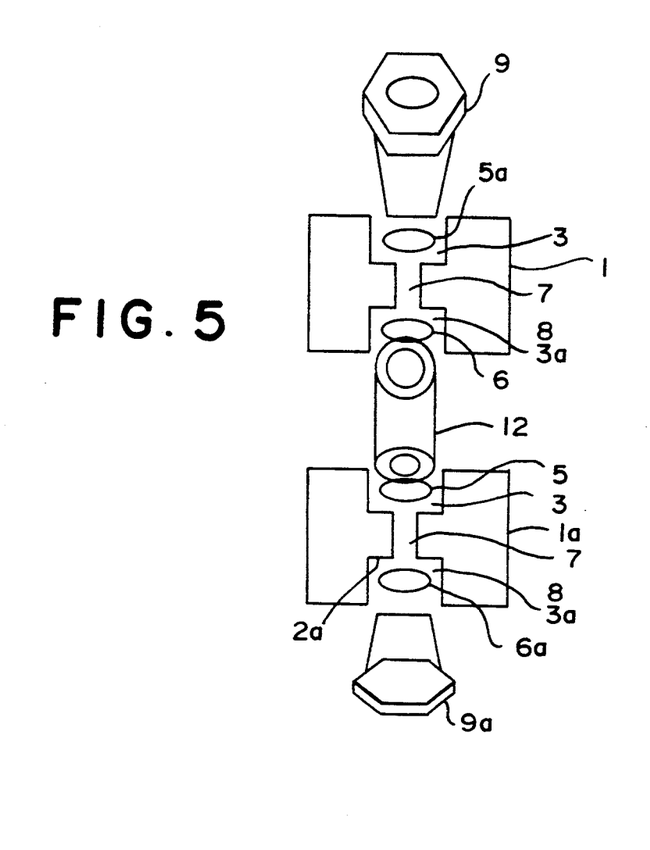
FIG. 5 shows an expanded view of a second embodiment according to the electroelution device of the present invention.

Referring to FIG. 5, an electroelution device is shown which contains multiple chambers 1 and 1a. In this embodiment, a screw 12, in which both ends are tapered, is used to join chambers 1 and 1a. Screw 12 is designed to fit into holes 3 and 3a as are screws 9 and 9a, which are made of similar materials. Screw 12 can join two together two slution chambers. Now membranes 5, 6 and membranes 5a, 6a can have different molecular weight cutoffs and can be inserted in the chamber to separate various macromolecules. In some applications, the gel can be inserted in hole 8 without having membrane 5.

Figure 6:
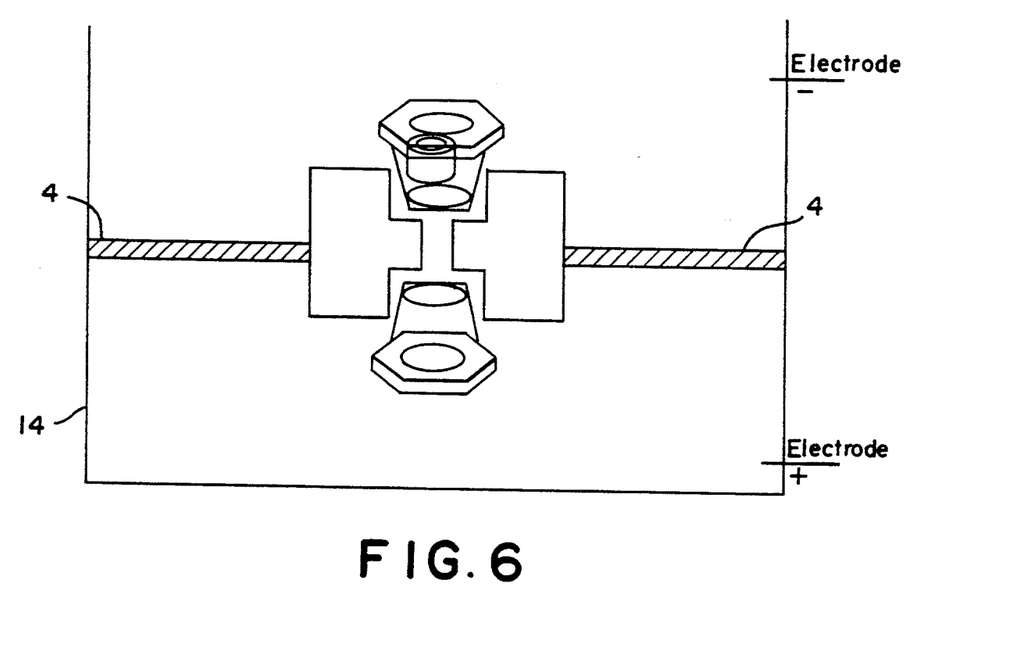
FIG. 6 shows an electrophoresis tank containing the electroelution device according to the present invention.

The electroelution device according to the present invention can also be used as a dialysis unit. In this embodiment, membranes 5, 6 are the same and have a molecular weight cutoff lower than the molecule. In this embodiment, screw 13 shown in FIG. 1 is utilized. Furthermore, the elution chamber 1 with membranes can be kept in a vacuum for further concentration of the fluid in hole 7. The chamber 1 will be attached to electrophoresis tank 14 (FIG. 6) by either the angle sealing plate 4, a gasket or with an O-ring.

Figure 7:
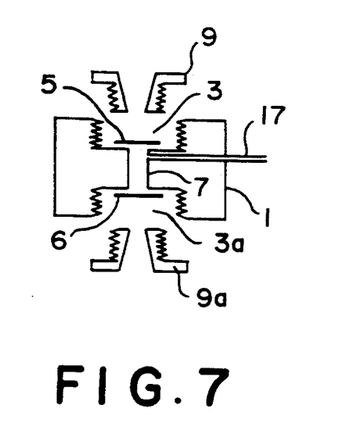
FIG. 7, 8 and 9 depict further embodiments of the electroelution device in accordance with the present invention.
Figure 8:
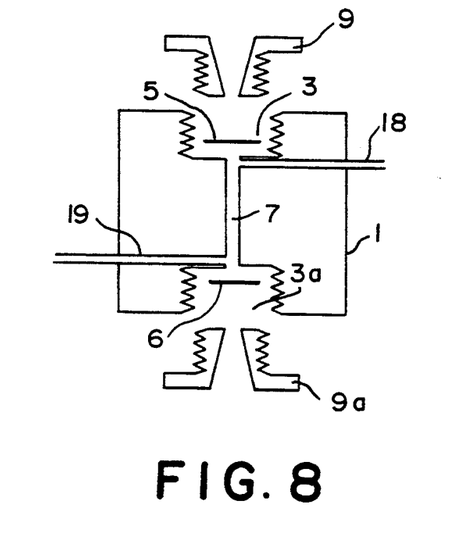

The chamber 1 can be provided with a very fine, small hole or aperture (e.g. about 1 mm in diameter) at the top portion thereof, as shown in FIG. 7. This hole has certain advantages, e.g. during the application of a high voltage, there is a possibility of the formation of an air bubble, which can stop or otherwise impede the flow of current. The small hole helps to remove the air bubble, and, because the hole dips in the same upper buffer, the biomolecule does not move through small hole due to current in the same direction. The chamber can also be provided with a plurality of openings 18, 19, as shown in FIG. 8. This modification has certain advantages: 1) No air bubble formation; 2) no clogging of membrane as the biomolecule is in circulation; and 3) large volumes of sample can be used without changing the chamber size.

Figure 9:
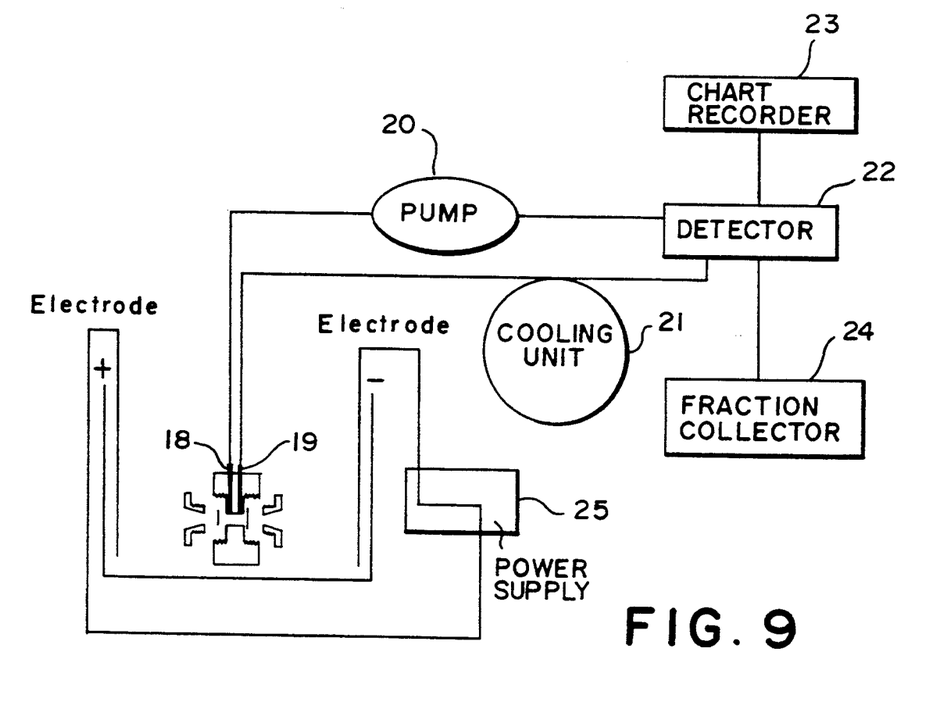
Figure 10:
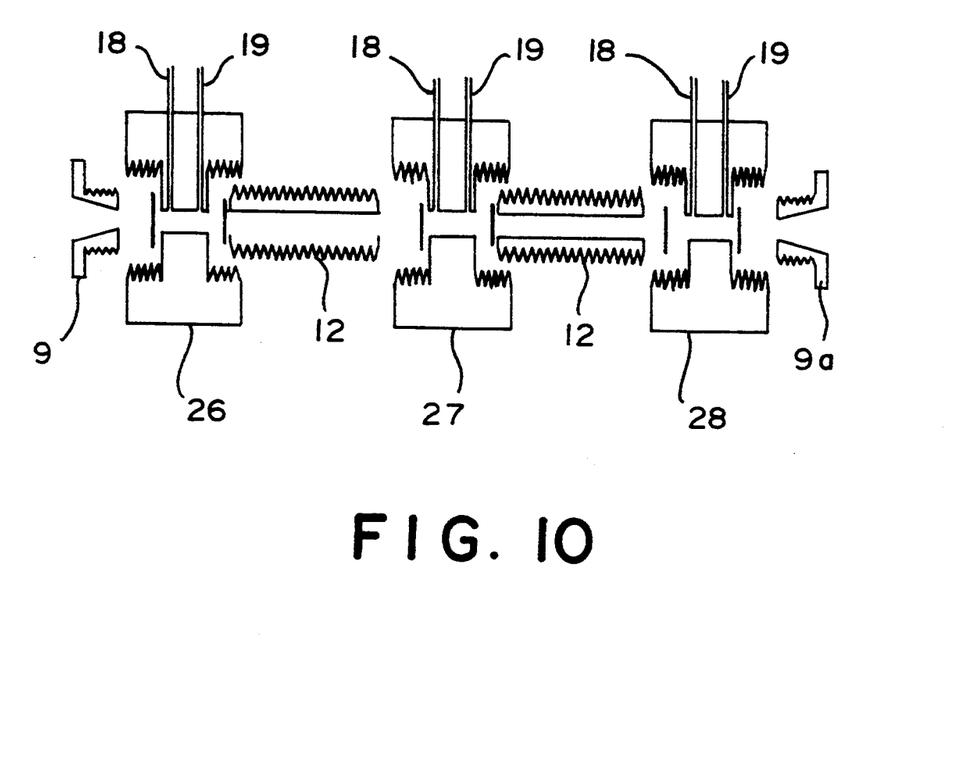
FIG. 10 illustrates serial interconnection of electroelution apparatus in accordance with the present invention.

A further advantage of providing the chamber 1 with a plurality of holes 18 and 19 is the capability of providing on-line monitoring of slution or purification of a sample using a detector 22 (e.g. a photometer for protein 280 nm, for DNA 260 nm), as shown in FIG. 9. The conductivity measurement can be used for monitoring for the removal of salts or exchange of buffers. With reference to FIG. 9, the holes 18 and 19 provide interfaces, respectively, to a pump 20 and coding unit 21 which are coupled to the detector 22. The detector, in turn, is coupled to a chart recorder 23 and a fraction collector 24. A power supply 25 is coupled to the electrodes. Finally, multiple chambers 26, 27 and 28 can be used for selective membrane purification, as shown in FIG. 10.

Figure 11:
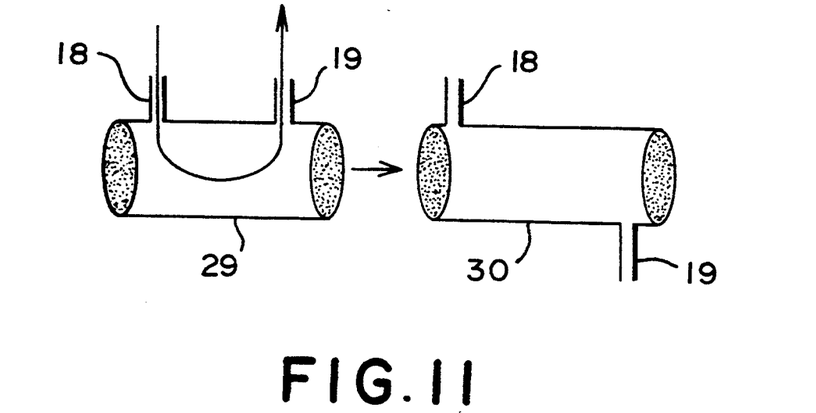
FIG. 11 shows electroelution devices having fused chambers in accordance with the present invention.

Fused membrane chambers 29 and 30 are depicted in FIG. 11. These chambers are used as disposables, i.e., a new chamber is needed for each application.

Figure 12:
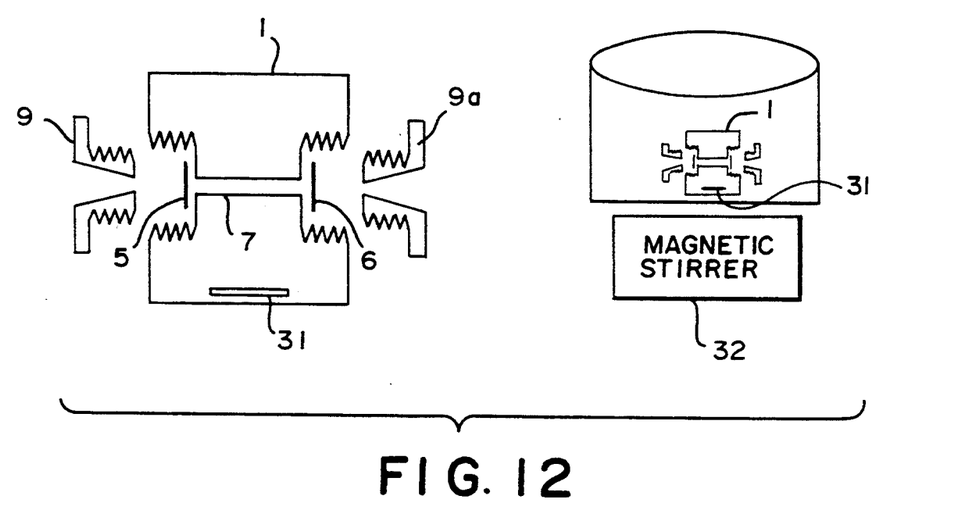
FIGS. 12 show an electroelution device having a magnet disposed in the chamber thereof in accordance with the present invention.

With reference to FIG. 12, a magnet 31 can be placed inside the chamber wall in such a way that it has no contact with the liquid. This chamber and magnet arrangement spins when placed in a magnetic stirrer 32 for dialysis or exchange of buffer. The magnet arrangement depicted in FIG. 12 is advantageous because the centrifugal force created by the stirrer 32 and magnet 31 interaction accelerates the exchange of molecules at the membranes 5, 6.

The operation of the electroelution device is illustrated by the following example, which is intended to be only illustrative in nature and not limiting.

FIG. 1 is an exploded view of the entire electroelution apparatus. FIG. 2 shows the joining of the two chambers 1 via screw 12. Gel or membrane holder 11 is employed to hold the PVDF membrane or other gel matrix.

Further objects and advantages of the invention will be revealed from the specifications and the enclosed drawings, which are for illustrative purpose only.

EXAMPLE #1

Problem: Elution of a protein of molecular weight 50,000 Daltons, amount 10 ug.

A 100 ul chamber 1 will be taken. A membrane 5 with a molecular weight cut off of 300,000 should be taken. This will serve as the top membrane. The bottom membrane 6 will have a molecular weight cutoff lower than the protein, e.g. 10,000. First put membrane 6 and tighten with screw 9a and then fill the well 7 with the electroelution buffer. Put membrane 5 in such a manner so that no air bubble is trapped in well 7 and close tightly with the screw 9. Fill the wells 8, 8a with the buffer, and then place the whole unit in an electrophoresis tank 14. Both anode and cathode compartments contain 50 mM Tris buffer, pH 8.3. A small piece of gel containing the protein $10 \times 5$ mm) is placed in side well 8 (or use holder 11 which can also hold the gel piece or PVDF membrane or other matrix). The electrophoresis chamber lid was closed, current (200 Volts/10 mA) is passed for about one hour. The protein is transferred in to well 7. If required, the Tris buffer can be exchanged by dialysis against a desired buffer by closing the chamber 1 either after replacement of membrane 5 by 10,000 molecular weight cutoff membrane or removal of the membrane 5, and closing using screw 13 which has no through-hole. If the sample is required to be concentrated, the chamber 1 can be put under vacuum.

EXAMPLE #2

Problem: PCR Products Purification

Polymerase chain reaction (PCR) is typically used for the amplification of DNA molecules. After the amplification of DNA, the primers are removed by a centrifugation method, by ion exchange or different columns, or by gel electrophoresis. These methods ordinarily require about 60-90 minutes for purification of DNA. The chamber described in accordance with the present invention can be filled with the PCR-reaction product, and at both the ends, a membrane is placed with a molecular weight cutoff larger (MWCO) than the primer of PCR reaction mixture. The whole chamber can be placed in any commercially available electrophoresis tank, without a gasket and with the buffer used for the electrophoresis of DNA. A current is passed for about 5-10 min., the primer is removed completely, and pure DNA is obtained for further sequencing or applications. This method is advantageous because it is fast (5-10 min.), requires only one step purification of nucleic acids (DNA, RNA), (e.g., no centrifugation, column chromatography or precipitation is required), and there is no change in volume. Furthermore, the method allows for high recovery, removes enzymes and salts if proper MWCO is chosen, and is autoclavable. Samples can be concentrated by using two chambers of different size and membranes of different pores. Furthermore, the same method is used for the slution of DNA from Gel, the removal of CsC1 after density gradient purification of DNA, the removal of Ethidium Bromide from DNA sample, and the removal of Gelass or Agragase and hydrolyzed fragment of agarose gel.

EXAMPLE #3

Problem: Concentration of Samples

Figure 13:
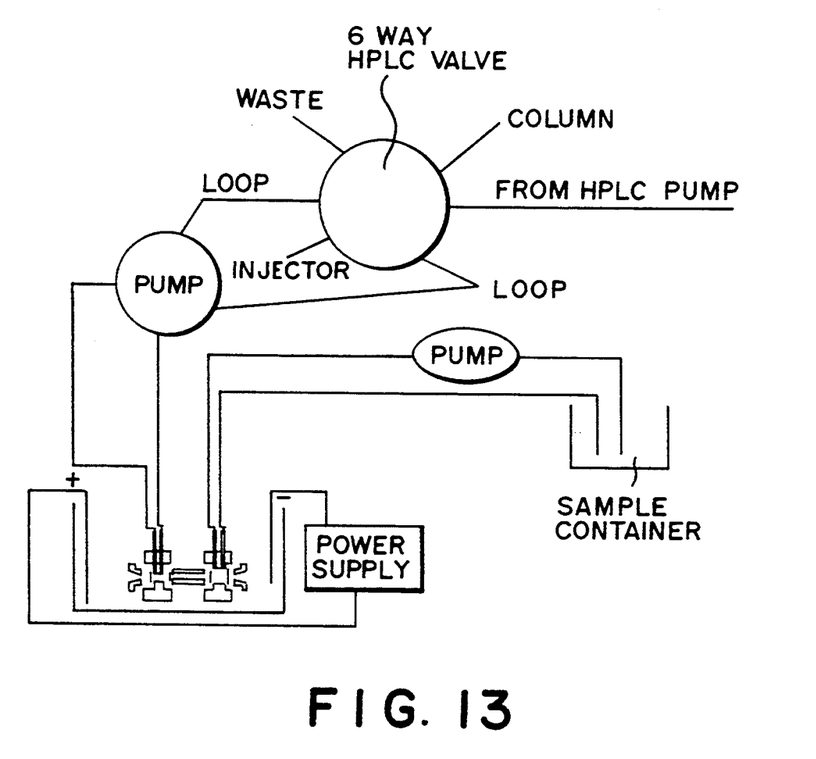
FIG. 13 shows an electroelution device used in connection with an HPLC valve in accordance with the present invention.

Charged molecules can be concentrated by electrodialysis. Chambers of different volume are used for the concentration of samples. A sample can be placed in large volume chamber, the whole unit assembled as in FIG. 5 and placed in an electrophoretic tank with a gasket. The buffers are used according to application. A current is passed and in such a direction that the biomolecule moves from the larger chamber to the smaller chamber according to the charge of the molecule. Within 5-10 min., most of the sample concentrates in the smaller chamber. By using through flow chambers, a continuous concentration can be achieved. Also, using preparative volume chambers, even large scale samples can be concentrated. Before injecting the sample in HPLC, the sample can be concentrated, desaired, or partially filtered using appropriate membrane or by using through flow cell chambers in combination with an HPLC injection valve. This method can also be used in combination with the autosampler of HPLC. FIG. 13 shows an electroelution device used in connection with an HPLC valve in accordance with the present invention. (FIG. 13.)

EXAMPLE #4

Problem: Multiwell Enzymic Reactions

Through flow chambers can be joined in series, as shown in FIG. 10 for the multienzyme reactions for identification of different charged molecules. With reference to FIG. 10, chamber 26 is filled with a sialoglycoconjugate and sialidase, an enzyme which removes sialic acids from sialoglycoconjugates. As soon as the sialic acid is released, it migrates to chamber 27, due to the electric field. Chamber 27 contains another enzyme which cleaves sialic acid to mannosamine and pyruvate. The pyruvate will migrate to chamber 28 where it could be detected by another enzyme followed by a photometer or a biosensor which is placed in chamber 28. By this method, different multienzyme reactions can be monitored in a more specific and selective manner than the multienzyme reactions in one container. Several advantages are realized. For example, different pH—optimums can be used for different enzymes. Therefore, the amount of enzyme used is much lower than the enzyme used in one container, where buffer could be good for pH optimum of one enzymic reaction and not for all enzymes used. Also, the product formed is migrated to another chamber and no auto inhibition is possible. Finally, further purification can be done with affinity chromatography.

EXAMPLE #5

Problem: High Salt Barrier (HSB) electroelution:

The invention as depicted in FIGS. 3 and 4 can be used for purification of DNA or proteins by high salt barrier method. This method is patented by Biometra GmbH, Germany. The chamber is generally fixed into a tank. In accordance with the present invention, the chamber can be removed from the tank and is advantageous because it is easy to clean, autoclavable, made of Teflon, and allows high recovery. In addition, different volumes of chambers can be used. Membranes can be used at both the ends or at one end.

OBJECTIVES AND ADVANTAGES OF THE INVENTION

The principle objective of the invention is to provide a one-piece apparatus in which to electrophoretically elute macromolecules and later dialyze the sample to any desired volume in the range of 10 ul to ml. Such samples would be free from salts, metal ions, unbound radioactivity and/or other contaminating material. Additional objectives and advantages of the invention are described below.

First, an objective is to provide a gel holder 11 of Teflon or any plastic material that can hold pieces of gel (for example, 10 mm×5 am or any other desirable size) containing the macromolecule and macromolecules transferred to PVDF or nitrocellulose or any other support. Since the amount of macromolecule to be eluted from the matrix is usually small (1-20 ug), the use of holder 11 disallows loss of recovery sample and targets its electrophoretic migration into the well 7.

A further objective is to provide a separator which includes two parts. The top well 8 serves to house the solid phase matrix to which the macromolecules are bound. The screw 9 is separated from the chamber 1 by an inert membrane disc 5 that has a molecular weight cutoff higher than the molecular weight of the macromolecule.

It should be clear from the above that molecular weight exclusion provides at least two advantages: i) the user is free to choose a membrane of any molecular weight cutoff required to elute the macromolecule, ii) if the gel matrix contains other macromolecules (e.g., a western blot containing a protein molecular weight of 50,000 and immunoglobulin G (IgG) molecular weight of about 180,000) then IgG can be retained on the membrane disc whereas the 50,000 molecular weight protein will pass through the membrane resulting in further purification of the 50,000 molecular weight protein.

Another objective of the invention is to provide a chamber 1 for macromolecules into which the macromolecule sample is collected. The advantage of this invention is to provide the user with the option to choose a desired volume in which the macromolecule will be suspended. For example, the user may wish to choose 10 ul to 1 ml as the final volume of sample. We assure the user such capability by providing a chamber 1 precisely to hold 10 ul to 1 ml. This is a very important feature of the invention, since often the amount of macromolecule bound to the matrix is in quantities of a microgram or less. As described above, elution and concentration by dialysis of such macromolecules results in considerable loss of material.

An additional objective of the invention is to pursue dialysis of the macromolecule sample contained in chamber 1. This is achieved by simply unscrewing the screw 9 from dialysis chamber 1. An obvious advantage of this invention is to provide the user with: i) an option to dialyze the sample without transferring into another container (no manual handling required); ii) a choice of buffer against which the sample may be dialyzed that is optimal for the procedures to be subsequently followed, iii) the option to predetermine the volume of the dialysate, for example 10 ul to 1 ml.

An additional objective of the invention is to provide a conventional filter 6 which is capable of entrapping the macromolecules in suspension, but which allows the free flow of molecules with low molecular weight such as sucrose, salt and chemicals (e.g., sodium dodecyl sulphate) and stains such as Coomassie Blue. The advantages of this device are: i) the user has a option of choosing membranes of a wide molecular weight range, resulting in removal of undesired molecules, ii) this membrane device is air-tight disallowing any leakage of the macromolecules. Finally the user removes the macromolecules from the chamber 1 by puncturing the membrane with a fine point needle and withdrawing the sample from the well 7 into a syringe. There are several advantages: i) No cross contamination of the sample with other solution during collection; ii) no manual handling for removal of buffers and membranes is required prior to the collection of the sample; iii) no removal of salts, unbound radioactivity and other contaminating samples is required.

Another objective of the invention is to provide a detachable screw 9, 9a to hold the membrane 5, 6 within the well 3, 3a. The advantages of this device are: i) to juxtapose the membrane 5, 6 against the chamber 1 keeping it air-tight, ii) to allow maintenance of a constant volume 7 within the chamber 1, and iii) the single-edge screw can be replaced with a double-edge screw 13 (FIG. 1). This can be used to attach another chamber 1a to hold membranes and to separate and concentrate yet another protein. Based upon these possibilities, it may be possible to pursue separation and concentration of proteins with grossly different molecular weights.

Another option of the invention is that the slution chamber alone can be used as dialysis unit for purification of macromolecule. However, if further concentration is required, the entire apparatus can be kept in a desiccator under vacuum to achieve the desired concentration.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. An electroelution device for the electroelution of macromolecules from a support, comprising a chamber and upper and lower releasably securable membrane retaining members, said chamber, and at least one of said upper and lower membrane retaining members having a through-hole for passage of a fluid, said chamber through-hole terminating at a membrane well at each of its ends and having a diameter less than that of said membrane wells, each of said membrane wells having a sidewall that is provided with a shoulder for receiving a membrane of a prescribed molecular weight porosity and a corresponding one of said membrane retaining members along a common axis such that the membrane is interposed between said shoulder and said membrane retaining member, said sidewalls and said membrane retaining members each having complementary-configured engagement surfaces for effecting engagement and retention of the respective membrane retaining members received therein.

2. The device of claim 1 wherein said membranes have molecular weight exclusions such that said macromolecules are retained within the through-hole of said chamber after electroelution.

3. The device of claim 2 wherein said membranes have different molecular weight exclusions.

4. The device of claim 1 which further comprises a holder for holding said support.

5. An electrophoresis tank containing the electroelution device of claim 1.

6. The electroelution device of claim 1 wherein the through-hole of at least one of said upper and lower membrane retaining members is tapered.

7. An electroelution device for the electroelution and separation of macromolecules from a support, the device comprising at least two chambers, a releasably securable upper membrane retaining member, a releasably securable lower membrane retaining member, and at least one connecting membrane retaining member, at least one of said upper and lower membrane retaining members, each of said chambers, and said connecting membrane retaining member each having a through-hole for passage of a fluid, the chamber through-holes having a diameter that exceeds that of the membrane retaining member through-holes, said chambers defining a membrane well at each end of said chamber through-hole having a sidewall that is provided with a shoulder for receiving a membrane of a prescribed molecular weight porosity and a corresponding one of said membrane retaining members along a common axis such that the membrane is interposed between said shoulder and said membrane retaining member, said sidewalls and said upper and lower membrane retaining members each having complementary-configured engagement surfaces for effecting engagement and retention of the respective membrane retaining members received within their corresponding membrane wells.

8. The device of claim 7 wherein said membranes have molecular weight exclusions such that said macromolecules are retained within the through-holes of said chambers after electroelution.

9. The device of claim 8 wherein said membranes have different molecular weight exclusions.

10. The device of claim 7 which further comprises a holder for holding said support.

11. An electrophoresis tank containing the electroelution device of claim 7.

12. The electroelution device of claim 7 wherein the through-hole of at least one of said upper and lower membrane retaining members is tapered.

13. A process for the electroelution of macromolecules from a support, comprising:

providing an electroelution device having a chamber and upper and lower membrane retaining members releasably securable within membrane wells formed int he chamber, the chamber and at least one of the membrane retaining members defining a through-hole for passage of a fluid, the membrane wells each including a sidewall having a configuration complementary to that of the membrane retaining members to engage and retain the membrane retaining members upon insertion into the wells and a shoulder for receiving an electroelution membrane of a prescribed molecular weight porosity and a corresponding one of the membrane retaining members along a common axis such that the membrane is interposed between the well shoulder and the retaining member; inserting an electroelution membrane into at least one of said membrane wells;

inserting the electroelution device into an electrophoresis tank having a plate, a cathode and an anode;

inserting a support containing macromolecules to be separated into the through-hole of one of said membrane retaining members; and applying an electric current across said electrophoresis tank to effect electroelution of said macromolecules from said support into the through-hole of said chamber.

14. The process according to claim 13, wherein the electroelution device comprises at least two chambers having membrane wells that are interconnectable by a connecting membrane retaining member, each of said chambers and said connecting membrane retaining member being provided with a throughhole for the passage of a fluid.

15. An electroelution device for immersion in an electrophoresis tank for the electroelution of macromolecules, said device comprising one or more chambers releasably sealable by an upper screw cap and a lower screw cap, each of said chambers and one (but only one) of said screw caps each having a through-hole for the passage of fluid.

16. A device as in claim 15, further comprising a magnet encased within said device for interaction with an external magnet to impart spinning motion to said device.

17. A device as in claim 15 comprising at least two chambers.

* * * * *